US00PP11856P2

(12) United States Plant Patent
Fleming et al.

(10) Patent No.: US PP11,856 P2
(45) Date of Patent: May 1, 2001

(54) *EUONYMUS FORTUNEI* PLANT NAMED 'BUSHEL OF GOLD'

(75) Inventors: David W. Fleming; Gretchen A. Zwetzig, both of Lincoln, NE (US)

(73) Assignees: Fleming's Flower Fields, Inc.; David Fleming; Gretchen Zwetzig, all of Lincoln, NE (US)

( * ) Notice: Subject to any disclaimer, the term of this patent is extended or adjusted under 35 U.S.C. 154(b) by 0 days.

(21) Appl. No.: 09/289,837

(22) Filed: Apr. 12, 1999

(51) Int. Cl.[7] ..... A01H 5/00
(52) U.S. Cl. ..... Plt./246
(58) Field of Search ..... Plt./246

*Primary Examiner*—Bruce R. Campell
*Assistant Examiner*—Wendy A Baker

(57) ABSTRACT

A new and distinct cultivar of dwarf, winter hardy *Euonymus fortunei* named 'Bushel of Gold' which is an extensively tested sport. This new and distinct cultivar is characterized primarily as to novelty by it's extreme cold hardiness to Zone 4, its golden yellow stems and foliage of a compact nature, its dwarf stature and its uniform and vigorous growth habit.

2 Drawing Sheets

BACKGROUND OF THE NEW PLANT

The new plant of this invention is the result of a unique hybridization, with the breeding acheivement being evidenced in the outstanding combination of characteristics exhibited by this new and distinct Euonymus plant, which include:

(a) A stable golden yellow coloring covering the compact foliage and stems entirely in full sun conditions; this is replaced by a chartreuse hue in partshade and in the winter.
(b) A plant with good vigor and disease resistence; and
(c) A plant with a dwarf and compact appearance similar to the parent plant, but improved in uniformity and compactness compared to many on the market.
(d) The plant being so hardy and heat tolerant that it can consistently withstand winter temperatures of at least −30 degrees Fahrenheit and summer temperatures of 100 degrees Fahrenheit.

SUMMARY OF THE INVENTION

'Bushel of Gold' is the result of a 40-year breeding program. It's ancestry includes the unpatented dwarf, decorative bush named 'Emerald 'n Gold' (U.S. Plant Pat. No. 2,231) developed by the Corliss brothers. More specifically the plant resulted as a naturally occurring branch sport of 'Emerald 'n Gold'. This plant was observed and tested for over 20 years (to be able to guarantee non-reversion of coloring) on the Fleming property.

This new plant was first discovered on the Fleming property in Lincoln, Nebr. in the summer of 1975 and was selected for the market by Gretchen Zwetzig and David Fleming. Asexual propagation of the plant by cuttings and tissue culture (specifically, micropropagation from apical meristems) in Lincoln, Nebr. has shown that the unique and distinguishing features of the plant are faithfully transmitted from generation to generation and appear to be firmly fixed.

Since its origin, this dwarf shrub has emerged with consistent yellow coloring and grown this way from spring until frost when it takes on a more chartreuse coloration; exhibiting also the above-mentioned characteristics. This hardy shrub contributes to the market with its striking appearance, its dwarf and very compact growth habit, its great resistance to disease and insects such as powdery mildew and other fungal diseases; aphids, spider mites and scale, it's stability through extremes in rain and drought, and its extreme hardiness.

BRIEF DESCRIPTION OF THE DRAWINGS

The foliage, stems and growth habit of the new perennial shrub are shown in the attached illustrations.

More specifically, the first drawing shows a picture which includes the entire plant from the front, taken at ground level.

The second drawing is a picture of the young growth as the plant emerges in Spring. The colors illustrated are as true as is reasonably possible to attain in photographic illustrations of this type. The colors may be slightly off due to light reflectance.

DESCRIPTION OF THE NEW PLANT

What follows is a detailed description of the new cultivar. The specific color designations set forth by PLATE number designations are in accordance with the *Dictionary of Color* (Maerz and Paul), while general color recitations are consistent with ordinary American color terminology.

'Bushel of Gold' has not been observed under all possible environmental conditions. It is to be understood that the phenotype may vary significantly with variations in environment such as temperature, light intensity, and day length, without, however any difference in genotype of the plant. The following botanical characteristics and observations are taken from a year-old plant when grown under normal outdoor conditions in Lincoln, Nebr.

THE PLANT

Parentage: A sport of the unpatented *Euonymus fortunei* 'Emerald 'n Gold' by the Corliss Brothers.

Form: Compact, rounded and dense, similar to the parent plant.

Growth: Mature plants are approximately 1½ feet tall. Plants reach a mature height, with an equal spread, in approximately two years.

Hardiness: Hardy to at least −30 degrees Fahrenheit.

Propagation: Easy, the tendency for the plant to turn "chartreuse" in the greenhouse makes chlorophyll absorption possible.

Stems: Dull and smooth; color is 'light chrome yellow' between L-3 and L-4 page 43, PLATE 10. In winter, the color is L-3, page 45, PLATE 11.

Auxillary buds: Compact, conical.

Foliage:

*Type*.—Broadleaf evergreen, petioled opposite.

*Shape*.—Ovate to elliptical.

*Apex*.—Obtuse.

*Base*.—Rounded to cordate.

*Margin*.—Crenulate.

*Petioles*.—Length approximately 2 mm; color is L-4, page 43, PLATE 10. In winter the color is L-3, page 45, PLATE 11.

*Size of leaf*.—Length is about 1½ cm; Width is about 1¼ cm.

*Leaf texture*.—Leaves are flat and have a smooth, glossy surface; they are not overly thick or leathery, but sturdy.

*Leaf veining*.—A bit lighter than L-3, page 43, PLATE 10; In winter, J-2, page 57, PLATE 17.

*Leaf margins*.—Slightly crenate.

Color:

*Entirety of upper surface*.—L-3 and L-4, page 43, PLATE 10.

*Underside of leaves*.—k-3, page 43, PLATE 10.

*Color of leaves when season is changing from late fall to winter*.—L-3, page 45, PLATE 11.

*Color of plant in winter and greenhouse state:* (*and color of young leaves*).—L-4, page 59, PLATE 18.

*Very bottom leaves of plant in shade*.—L-6, page 71, PLATE 24.

*Fruit/seed*.—To date, the plant has not been observed to bloom or to set fruit or seed.

GENERAL OBSERVATIONS

This shrub, as a sport-originating Euonymus plant, is valuable to the landscape market for its improvements in dwarfness, brilliantly colored yellow, compact foliage, good vigor, adaptation to extreme environments, including the ability to survive winter temperatures of at least −30 degrees Fahrenheit, and from a distance, all of this combing to give 'Bushel of Gold' a striking "spotlight" appearance in the garden.

We claim:

1. A new and distinct cultivar of Euonymus bush, as herein shown and described, characterized by its dwarf nature and compact growth habit, its bold golden-yellow foliage and stems in summer, its pleasant chartreuse coloring in winter, its vigor, and its hardiness.

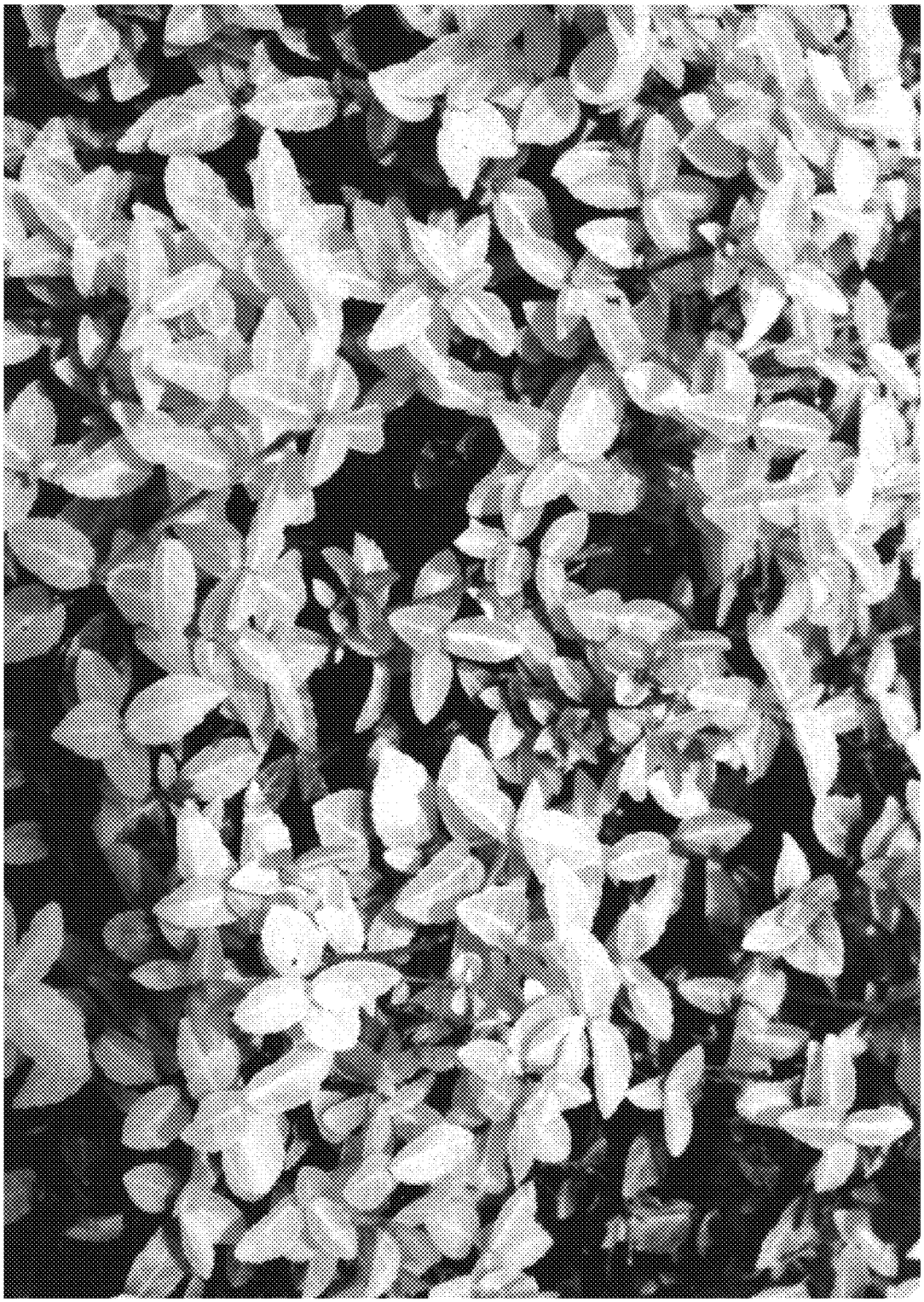

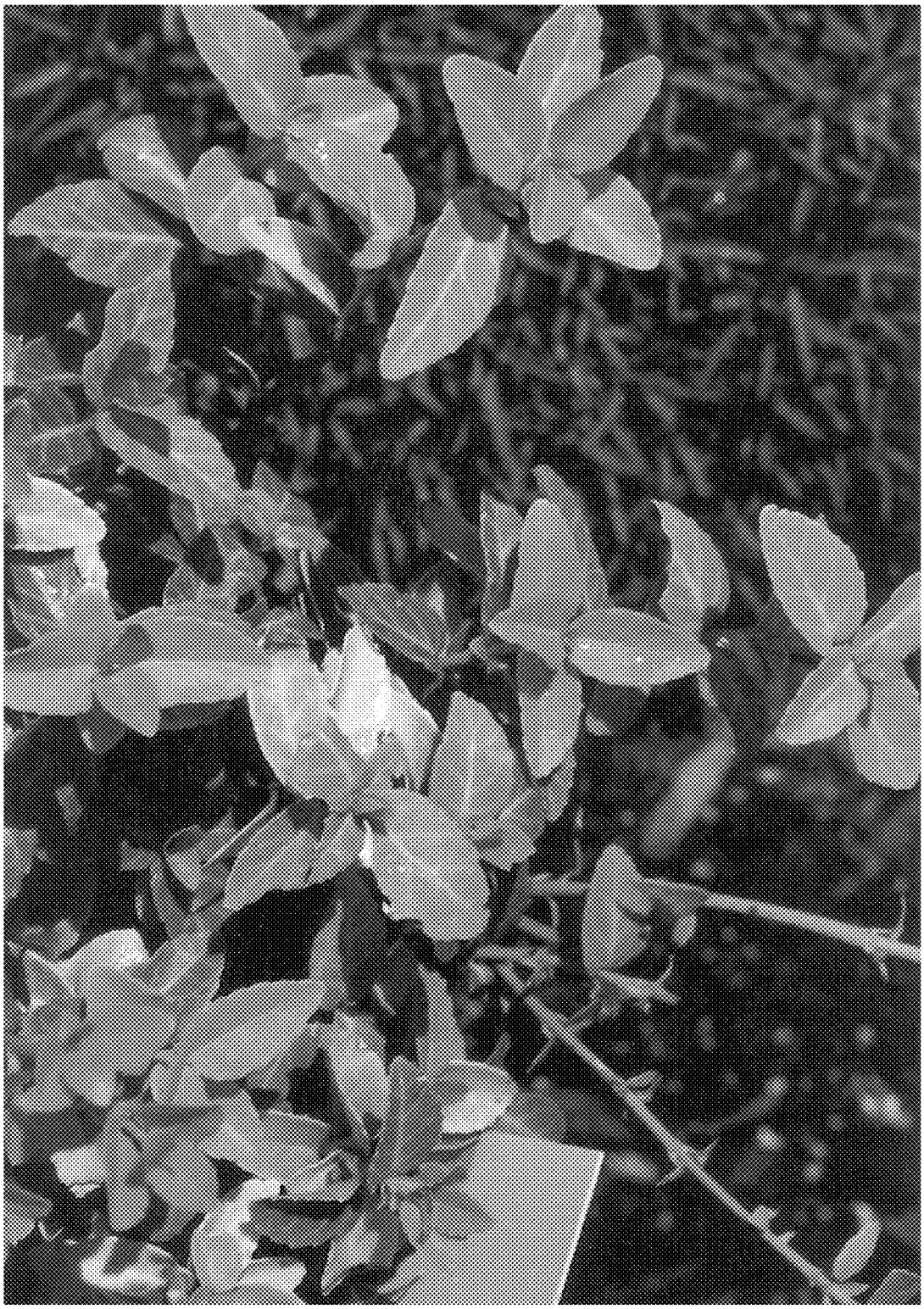

* * * * *